United States Patent [19]

Woodroof

[11] Patent Number: 4,820,302

[45] Date of Patent: Apr. 11, 1989

[54] BIO COMPATIBLE AND BLOOD COMPATIBLE MATERIALS AND METHODS

[75] Inventor: E. Aubrey Woodroof, Santa Ana, Calif.

[73] Assignee: Sterling Drug Inc., New York, N.Y.

[21] Appl. No.: 392,018

[22] Filed: Jun. 25, 1982

Related U.S. Application Data

[63] Continuation-in-part of Ser. No. 370,977, Apr. 22, 1982, abandoned, which is a continuation-in-part of Ser. No. 5,319, Jan. 22, 1979, abandoned.

[51] Int. Cl.$^4$ ............................................. A61F 2/52
[52] U.S. Cl. ...................................................... 623/8
[58] Field of Search ................ 3/36, 1; 128/155, 156, 128/DIG. 8; 424/DIG. 13; 427/2; 435/178; 523/105, 111, 112, 113

[56] References Cited

U.S. PATENT DOCUMENTS

| | | | |
|---|---|---|---|
| 3,457,098 | 7/1969 | Leininger | 117/62.1 |
| 3,617,344 | 11/1971 | Leininger | 3/1 |
| 3,639,141 | 2/1972 | Dyck | 427/2 |
| 3,846,353 | 11/1974 | Grotta | 260/9 |
| 3,955,012 | 5/1976 | Okamura et al. | 427/2 |
| 3,986,213 | 10/1976 | Lynch | 3/36 |
| 4,001,583 | 1/1977 | Barrett | 250/303 |
| 4,060,081 | 11/1977 | Yannas | 128/DIG. 8 |
| 4,243,776 | 1/1981 | Marconi et al. | 523/112 |
| 4,329,383 | 5/1982 | Joh | 3/1 |

FOREIGN PATENT DOCUMENTS 2139455  2/1972  Fed. Rep. of Germany .......... 427/2

OTHER PUBLICATIONS

Orchin et al. (Orchin), *The Vocabulary of Organic Chemistry,* John Wiley & Sons, New York, pp. 75–76 (1980).

*Primary Examiner*—Richard J. Apley
*Assistant Examiner*—Alan Cannon
*Attorney, Agent, or Firm*—Beehler, Pavitt, Siegemund, Jagger, Martella & Dawes

[57] ABSTRACT

Bio- and blood compatible materials are prepared by treating the surface of a substrate to provide reactive primary or secondary amine groups sites which are activated by treatment with a dialdehyde or arylchloride for coupling to a biological in an amount sufficient to provide compatibility. The use of specific substrates, such as a compliant, and elastic material, such as a fabric-elastomer membrane matrix, results in a product having advantageous qualities as a thermal burn dressing, breast prostheses and implants. Detailed procedures and various products are described.

10 Claims, No Drawings

BIO COMPATIBLE AND BLOOD COMPATIBLE MATERIALS AND METHODS

RELATED APPLICATIONS

This application is a continuation-in-part of U.S. application Ser. No. 370,977 filed Apr. 22, 1982, now abandoned, which in turn is a continuation-in-part of U.S. application Ser. No. 005,319 file Jan. 22, 1979, now abandoned.

BACKGROUND OF THE INVENTION

This invention relates to bio-compatible and blood-compatible materials and their method of preparation and more particularly to an improved bio-compatible and compliant material of the type described which may be topically or internally applied or contacted by biologicals, blood, or tissue, as, for example, a burn dressing, a surgical dressing, a cardiovascular graft or implant material, and the like, and to the method of making the same.

There are many instances in medicine in which there is a need for a bio- and blood-compatible material for human and animal use and for use in equipment contacted by biologicals or blood, e.g., tubing, containers, valves, etc. For example, in extra-corporeal circulation of blood, i.e., heart or artificial kidney there is a tendency for blood to coagulate on contact with a "foreign surface", see, for example, U.S. Pat. Nos. 3,642,123 and 3,810,781. Also, products such as heart valves, materials used in coronary and vascular grafts, and catheters, oxygenator tubing and connectors tend to cause thrombosis of the blood.

In addition to the above, materials used as burn dressings and surgical dressings should be bio- and blood compatible. In the case of such dressings, an area in which the present invention finds particular utility, there are additional requirements because of the use of the materials.

As is known in the art, and described in U.S. Pat. No. 3,800,792, treatment of second and third degree burns involves a number of phases, including cleaning and stabilizing the wound area to the development of a granulation bed at the wound site. The final phase of treatment is usually the autografting phase which sometimes takes place some period of time after development of the granulation bed. The maintenance of the granulation bed is a necessity until such time as autograft is available and successful autografting is completed.

Several different approaches have been used to preserve the wound site, i.e., granulation bed, for example, application of wet dressings which must be changed frequently and tend to add to patient discomfort. Homografts, heterografts and synthetic dressings have also been used.

Accordingly, a wide variety of dressings, characterized as biological and synthetic, have been used in the treatment of burn wounds. Biological dressings include any dressing that has one or more biological components, i.e., protein, carbohydrates, lipids and the like. Presently, homograft and porcine xenograft skin are dressings currently used to maintain the granulation bed.

In burn patients with large areas of burn tissue, the amount of available skin (autograft) is limited and temporary dressings are required for long periods of time to maintain the granulation bed. Homografts (cadaver skin) is the current dressing of choice, when available. Unfortunately, homograft has a limited shelf life and is relatively expensive, i.e., $85.00 to $90.00 per square foot. Human amniotic membrane has also been used but is less desirable than cadaver skin. Lack of availability and short shelf life are also drawbacks.

Xenograft (porcine) skin is commercially available but is considerably less effective than homografts and autografts. Short shelf life, sterility and limited application are known disadvantages of this material, in addition to an antigenicity problem.

DESCRIPTION OF THE PRIOR ART

In addition to the materials previously mentioned, various forms of collagen have been used in the treatment of burns, see U.S. Pat. No. 3,491,760 which describes a "skin" made from two different tanned collagen gel layers.

U.S. Pat. No. 3,471,958 describes a surgical dressing made up of a mat of freeze dried microcrystalline collagen, while British Pat. No. 1,195,062 describes the use of microcrystalline colloidal dispersions and gels of collagen to produce films which are then applied to various fibers such as polyurethane.

A "biolization" process for improving the blood and biocompatibility of prosthetic devices has been described by Kambic, et al and others, see Trans. 3rd Annual Meeting Society for Biomaterials, Vol. 1, p. 42, 1977. Their methods involve deposition of gelatin into a rough textured rubber with subsequent cross-linking and stabilization of the gelatin with 0.45% gluteraldelyde.

Also of interest is U.S. Pat. No. 2,202,566 which describes collagen fibers in bandages and U.S. Pat. No. 3,113,568 which discloses the use of polyurethane foam in a bandage.

There are numerous references in the literature to various other materials used in burn treatment. For example, collagen membranes have been fabricated from suspensions of bovine skin and evaluated in a rat animal model. The adherence of this material was superior to auto- homo- and xenografts on full and split thickness wounds but inferior to auto- and homografts on granulating wounds, see Tavis et al, J. Biomed. Mater. Res. 9, 285 (1975) and Tavis et al, Surg. Forum 25, 39 (1974).

McKnight et al, developed a laminate of collagen foam with a thin polyurethane sheet, see U.S. Pat. No. 3,800,792. Film prepared from reconstituted collagen has also been used, Tavis et al, supra, and a commercially grade of such material is available from Tec-Pak Inc. Gourlay et al, Trans, Amer, Soc, Art, Int. Organs 21, 28 (1975) have reported the use of a silicone collagen composition, collagen sponge, and non-woven fiber mats.

Park, "Burn Wound Coverings–A Review", Biomat, Med. Dev. Art. Org. 6(1), 1–35 (1978) contains a review, with extensive literature citations, of various burn wound coverings, including laminates of velour fabrics such as nylon, dacron (polvster), rayon, Teflon and polypropylene. Velour silicon rubber laminate are reported with the observation that Teflon and polypropylene velours could be easily peeled off the granulation bed. Rayon appeared to adhere well but disappeared after 10 to 14 days leaving only the silicone rubber backing. Dacron and nylon appeared to adhere well.

Nylon velour incorporating polypeptide films and polycaprolactone films were criticized because of cracking of the film. Ultra thin silicone fabric composite membranes have been reported by Kornberg et al, Trans. Amer. Soc. Artif. Int. Organs, Vol. 18, pp. 39–44, 1972.

In the literature reports of some of the above materials, adherence, continued elasticity and flexibility, and water vapor transmission appeared to emerge as important parameters in burn dressings. Thus, as far as burn wound coverings the following characteristics emerge as desirable:

1. The material must adhere to the wound base (comparable to auto- and homograft) to minimize infection and sepsis.
2. It must have adequate flexibility over a period of time in order to cover joints and other areas of body flexion.
3. It must have the proper moisture vapor transmission rate to maintain proper moisture balance at the wound site.
4. It should be capable of being easily stored, sterilized and available for use on short notice for emergency procedures.
5. It must not be toxic, pyrogenic, or antigenic.
6. It should be readily available at reasonable cost.
7. It must be capable of being applied to the wound site so as to completely isolate the site.
8. It must have sufficient strength to be secured by sutures, clips and the like.

In addition to the above, U.S. Pat. No. 3,846,353 describes the processing of silicone rubber with a primary or secondary amine, see also Canadian Pat. No. 774,529 which mentions ionic bonding of heparin on various prosthesis.

In addition to the above, there is considerable literature relating to the use of silicone rubber membranes Medical Instrumentation, Vol. 7, U.S. Pat. No. 4,268,275 September-October 1973; fabric reinforced silicone membranes, Medical Instrumentation, Vol. 9, U.S. Pat. No. 3,124,128, May-June 1975. U.S. Pat. No. 3,267,727 also describes the formation of ultra thin polymer membranes.

It is also known that various materials may be heparinized, in order to impart a non-thrombogenic character to the surface of a material, see for example U.S. Pat. Nos. 3,634,123; 3,810,781; 3,826,678; and 3,846,353, and Canadian Pat. No. 774,529, supra.

In the case of implants, for example those used in subcutaneous implanted mammary (breast) prostheses, one of the problems widely discussed in both the patent literature and the medical literature including reference texts, is that of capsular contracture or constrictive fibrosis, sometimes referred to generically as fibroplasia.

As reported in the literature, surgical reconstruction of the human female breast by implantation of mammary prostheses has been performed for a number of years for cosmetic purposes and/or to replace one or both breasts previously removed in whole or in part as a result of disease or injury. Where all or a portion of a breast is removed because of disease, restoration of the natural contours of the body may be of psychological significance in assisting the patient in coping with the trauma associated with such surgery.

Mammary augmentation has many advantages and benefits, however, the implantation of a mammary prosthesis, for example, a pliable silicone gel-filled mammary implant having an outer silicone elastomer wall, or another form of such prostheses, results in the formation of a capsule around the prostheses. The literature to date seems clear that capsules do exist around the prostheses, possibly due to "foreign body rejection", (Vistnes et al "Study of Encapsulation of Silicone Rubber Implants in Animals. A Foreign Body Reaction." Plast. Reconstr. Surg. 62: 580, 1978). It is equally clear from the literature that not all capsules contract, Gayou et al, "Capsular Contraction Around Silicone Mammary Prostheses Overview" Ann. Plast. Surg. 2; 62, 1979.

The literature, however, is not in agreement as to the cause of contracture. The suggestion that it is caused by myofibroblasts e.g. a contractile cell which is transitional between fibroblast and smooth muscle cell (Rudolph et al, "Myofibroblasts and Free Silicone Around Breast Implants", Plast. Reconstr. Surg. 62:185, 1978) seems to be in dispute (Ginsbach et al, "The Nature of the Collagenous Capsules Around Breast Implants; Light and Electron Microscope Investigations", Plast. Reconstr. Surg. 64: 456, 1979).

Capsular contracture can occur in varying degrees and in the more severe cases, where spherical capsular contraction occurs, the implant contracts into a sphere which may become hard, has an unnatural appearance and may be quite painful. Gayou et al, supra, reports the various preventative measures which have been taken and the results achieved.

While the exact cause of abnormal induration of the prosthesis is not precisely known, see Vistnes et al, supra, various and different attempts have been made in the prior art to reduce the effect of contracture rather than to control the contracture and prevent it from occurring in the first instance.

Gayou et al, describes some of the prior procedures which have been used and also comments on their effectiveness. In addition, various approaches are described in the patent literature, for example, U.S. Pat. No. 4,298,998 of Nov. 10, 1981 to Naficy describes a prostheses which the capsule is caused to form in spaced relation a predetermined distance from the surface of the prostheses. The Naficy approach involves the use of an outer temporary component which is absorbed thus causing the capsule to form some distance from the outer surface of the inner core of the prostheses. Naficy also describes the prior efforts as reported in the literature and prior patents. Other patents which relate to structural modification of the prostheses include U.S. Pat. Nos. 3,934,274 issued to Hartley on Jan. 27, 1976; 4,095,295 issued to Lake on June 20, 1978; 4,205,401 issued to Frisch on June 3, 1980 and 4,264,790 issued to Hamas on May 5, 1981.

In addition to the above, there is a significant body of art dealing with mammary prostheses formed of a particular material, see for example Calnan et al, Brit. J. Plast. Surg., 24(2), pp. 113–124(1971); Walz, Med. Welt. 30(43), pp. 1587-94 (Oct. 26, 1979), and Bassler, Zeitschrift fur Plastische Chirurgie 3 (2), pp. 65-87 (July, 1979).

Also present in the art are disclosures of bio- and blood compatible substrates through the use of biofunctional surfaces. For example, Ratner et al, J. Biomed. Mater. Res., Vol. 9, pp. 407-422 (1975) describes radiation-grafted polymers on silicone rubber sheets. U.S. Pat. Nos. 3,826,678 (Hoffman et al issued July 30, 1974) and 3,808,113 (Okamura et al issued Apr. 30, 1974) describes the use of serum albumin and heparin as a biological coating, and collagen cross-linked by radiation. Collagen muco-polysaccharide composites are described by Yannas et al in U.S. Pat. No. 4,208,954 issued on July 28, 1981 while Yannas et al U.S. Pat. No. 4,060,081 of Nov. 29, 1977 describes a multi-layered membrane for control of moisture transport in which cross-linked collagen and muco-polysaccharide is said to preclude immune response. Eriksson et al in U.S. Pat. No. 4,118,485 of Oct. 3, 1978 describes a non-thrombogenic surface using heparin.

Other prior art approaches are represented by the reported work of T. Miyata in Advances in Chemistry, No. 145, pp. 26-35 (1975); Japanese Pat. No. Sho 46(1971)-28193 and Kogaku No Ryoiki, Vol. 28(b) pp. 469-76 (1974). The Miyata work generally involves the use of collagen (tropo-collagen and tropocollagen with portions of the teleopeptides remove) and mucopolysaccharides (heparin and hyaluronic acid) to make or coat various products such as arterial prosthesis, kidney dialysis devices and hollow fiber tubing and the like.

It is also known to use a high molecular weight collagen fraction as a biological for an artificial heart. The biological is precipitated and then cross-linked to an irregular rubber surface using glutaraldehyde. The result is not a flexible coating in that the biologicals are covalently bonded to each other and are physically entrapped in apertures in the rubber.

SUMMARY OF THE INVENTION

The product and process of the present invention differ from the prior art by providing a composite elastomeric material from a thin film of polymeric material (e.g., silicone rubber) and a knitted or woven fabric (e.g., nylon). The polymer component can be layered with high precision (final cured sample thicknesses with a tolerance of ±0.00025 inches). The fabric component (without wrinkles) and the composite is cured at a temperature of approximately 300° F. for 15-60 minutes. To this composite which may be an elastomeric matrix, one or more biological molecules such as proteins (collagen, gelatin, fibrinogen, egg albumin, human albumin, human gamma-globulin, or other animal or plant proteins), carbohydrates (acidic mucopolysaccharides, starch, simple sugars, etc.), lipids (lecithin, choline, unsaturated or saturated free fatty acids, other complex or simple lipids), amino acids (aspartic acid, lysine, glycine, serine, etc.), dipeptides (Glycylglycine and others), larger peptides and the like may be bonded using a number of commercially available reagents to accomplish either hydrophobic or covalent bonds. The process can be thought of as a final product of composition A, B, C. The "A" represents the elastomeric fabric-polymeric composite matrix, which provides ideal physical properties (e.g., elasticity, conformability and water vapor transport properties). The "B" represents one or more components used to bond the "C" component (one or more biologicals) to the "A" component (fabric-polymeric composite matrix. The completed product A-B-C is used to impart a specific quality or a combination of characteristics of the material)A-B-C) to render them bio- and blood compatible.

The materials of one embodiment of the present invention also exhibit a moisture vapor transmission rate, i.e., the weight of water lost by evaporation through a film membrane at 37° C. over a period of 24 hours, of about 10-15 grams per hour per meter squared or about 1-1.5 milligrams per hour per centimeter squared, which is a rate similar to human skin, however, the WVT property of these materials are subject to modification to optimize wound healing.

Where used as a burn dressing, which is the principal but not the sole use of the materials of this invention, the material exhibits a moisture vapor transmission rate in the range indicated and, because of the inclusion of biological components, exhibits good adherence to the burn area. Thus, the materials of the present invention, when used as a burn dressing, preferably is in the form of a laminate including a thin film of a polymer, i.e., silicone rubber, urethane or other elastomeric polymer material, the film of polymer being of such dimensions and composition as to have a water vapor transmission rate in the range indicated. Physically bonded to the thin polymer film is a thin porous fabric such that the composite is elastic in all directions, i.e. length and width. Covalently coupled to one or both sides of the laminate is one or more biological materials to provide adherence and compatibility to the wound site.

Regardless of the form of the substrate, sheet, tube, formed contour, and the like, the biological compound is bound by treating the substrate with a primary or secondary amine such that the amino groups are available for further reaction. In one form this is accomplished by incorporating the primary or secondary amine into the substrate such that the amino functional groups extend out of the surface as coupling sites. In another form, the substrate is coated with a primary or secondary amine silating agent in order to provide terminal available amino functional groups, again as coupling sites.

The first form above described is similar in part to the procedure described in U.S. Pat. No. 3,634,123 and the primary and secondary amines there disclosed may be used in this form of the present invention.

The second form above described offers the advantage of being able to provide available amino groups reactive sites with a variety of substrates both of organic and inorganic character, etc., substrates other than silicone, urethane, for example, other polymers to which the material will adhere, or to inorganics such as metal or glass.

The procedures thus far described are distinguishable from those of U.S. Pat. No. 3,846,353 which use a long chain alkyl quaternary ammonium salt to ionically bind heparin to various polymer substrates.

According to the present invention, the available amino functional groups are then activated for bonding to a biological. This is in contrast to U.S. Pat. No. 3,634,123 in which heparin is ionically linked to the positively charged amine directly, or in contrast to U.S. Pat. 3,810,781 which treats the substrate-amine hydrochloride-heparin salt subsequently with a dialdehyde, such as glutaraldehyde, to stabilize the heparin on the substrate surface.

Activation of the amino groups, according to the present invention, may be accomplished by one of several ways. In one form dialdehyde, such as glutaraldehyde, is reacted with the primary or secondary amine provided by either of the procedures described, leaving available aldehyde groups average of one per molecule of glutaraldehyde for subsequent reaction with the primary or secondary amines of either proteins, mucopolysaccharaides, or other amine containing biologicals. In another form, the preferred form, cyanuric chloride is reacted with the primary and secondary amines provided on the substrate as previously described. The remaining available chloride groups of cyanuric chloride may then be used to react with the primary or secondary amines or hydroxyl groups of various biologicals to form colvalent bonds.

Other bifunctional reagents that may be used to link substrate amines with biological amines are thiophosgenes, isocyanates, derivitized cyanuric chloride (one Cl group removed or alkylated), 1,5-difluoro-2, 4-dinitrobezene, diazobenzidine, toluene-2, 4-diisothiocyanates and others.

Thus, a wide variety of new, improved and relatively simple procedures are described for attaching various biologicals on a substrate which, in accordance with this invention, may be used as burn covering having the desirable properties mentioned.

In the case of implants for prosthesis use, the present invention represents a departure from the approach taken in the prior art, especially in the case of breast prostheses. More specifically, a biological is coupled to the portion of the prosthesis which ultimately comes into contact with host tissue and the like of the recipient in order to provide biological compatibility in the context of reducing what has been referred to as a foreign body reaction, see Vistnes et al, supra.

In particular, the improved prostheses for use as breast implants involves a unique chemical bonding system for the biological, which in a preferred form is present in an amount and in a form sufficient to provide biocompatibility. The chemistry used in bonding the biological is as generally described, however, in the case of devices used for breast prostheses, specific biologicals are used in preference to other possible candidates with the result that contracture appears to be reduced, or at least the rate of contracture is significantly slowed.

One of the advantages of this invention insofar as a breast prosthesis is concerned is that the prosthesis of this invention may be steam sterilized at any time prior to implantation without adversely affecting the activity of the bound biological. For example, some of the prior art biologicals can only be sterilized by ethylene oxide gas treatment in order to prevent denaturing of the biological. According to this invention, the prosthesis may be steam sterilized immediately before implantation, removed from the autoclave and maintained in a sterile area in the operating suite until used. This advantage appears to be of practical importance in light of the literature reports of the difficulty in achieving asepsis in implant procedure, see Gayou et al., supra. Moreover, it has been reported that residual or adsorbed ethylene oxide may cause an adverse tissue reaction if an elthylene oxide sterilized breast prosthesis is implanted prior to outgassing of any significant residual amount of ethylene oxide.

Another advantage of this invention is that it may be used with any of the breast prosthesis devices heretofore used, e.g., single lumen, double lumen devices, and the like and those with components attached to the outer surface of the implant, see, for example, Rybka, U.S. Pat. No. 4,298,997. The present invention may be used with any of the presently commercially available products including Silastic ® Mammary Implant (Gel-Filled), Silastic ® Varifil Implant (Inflatable type), Heyer-Schulte Gel-Filled Mammary Prosthesis, McGhan Medical Corporation Mammary Implant (Gel-Filled), and McGhan Intrashiel ® Mammary Implant, for example.

In a preferred form of this invention, the breast prosthesis includes all of the desirable qualities such as shape, feel, bounce and the like which tend to simulate the natural appearance of the natural breast, i.e., tactile and motile characteristics tending to simulare the natural appearance of the natural breast, but also includes an active outer surface which is biologically active and which tends to reduce significantly the rate at which contracture tends to take place. In a preferred form, the envelope of the prosthesis is soft, thin and seamless. The envelope may be a laminate of fluorosilicone with medical grade high performance silicone elastomer. The biological surface, in accordance with this invention, is preferably hypoallergenic, non-toxic, non-pyrogenic, hydrophilic and non-antigenic. Thus, for example, gel filled implants may be used, preferably of the single lumen type, although double lumen devices may be used, if desired.

It will be apparent from the following detailed description and specific examples and data that a much improved bio-and blood compatible material has been provided by a relatively simple and reliable procedure. The further advantages and features may be understood with reference to the following description of the invention.

DETAILED DESCRIPTION OF THE INVENTION

The present invention relates to bio- and blood compatible materials which may take various forms and shapes, for example, rigid and flexible tubes, sheets or formed and contoured shapes, for use in equipment and/or in patients. Since burn wound coverings, one form of the present invention, include the characteristics of adhesion to the wound site and elasticity in all directions, although it will be understood by those skilled in the art that the present invention is not limited to such dressings, but has applicability to bio- and blood compatible materials.

In general, the present invention relates to a novel and improved bio- and blood compatible material in which specific characteristics are imparted to a substrate by a novel, simple, effective and inexpensive procedure for covalently coupling to the substrate certain biological materials or combinations thereof. Typical of the biological materials which can be covalently coupled to the substrate are those which include an available primary or secondary amine reactive group which can react with an aldehyde group or arylchloride group (i.e., or cyanuric chloride or its derivative) and those which include an available hydroxyl group which can react with an arylchloride group. Representative materials are proteins, collagen, albumin, gelatin, fibrinogen, animal or plant proteins, complex carbohydrates (i.e., acidic mucopolysaccharides), simple carbohydrates, lipids (i.e., lecithin), peptides, and amino acids. Typical of the complex carbohydrates are heparin, hyaluronic acid, chronditin sulfate A (4 position) and C (6 position), to mention only a few.

Conceptually the improved and novel products of the present invention, produced by the improved and novel process of this invention, include a suitable substrate treated to provide available and reactive primary or secondary amine functional reactive sites. The amine functional sites are then activated either by reaction with a dialdehyde, or preferably cyanuric chloride to provide available active aldehyde or arylchloride groups, respectively. Thereafter, one or more biological materials, as previously described, having a hydroxyl, primary or secondary amine, is then coupled to the available free aldehyde or arylchloride group. In this way select biologicals are covalently coupled to the substrate in an amount and in a form sufficiently stable to provide bio- and blood compatibility to the substrate.

The usable substrates may be a wide variety of materials depending upon the procedure and to provide available primary and secondary amine functional reactive sites. For example, a reactive silane containing a primary or secondary amine may be used as a primer and coated on the substrate to provide the reactive amine group. Such a procedure is described in Canadian Pat. No. 774,529, however, the amine is then alkylated to form a positively charged quaternary ammonium salt which is then used to ionically bind heparin to the surface of the substrate.

Thus, typical substrates are glass, and the elastomers, silicone rubbers and polymers used in medical applications. Representatives of such materials are:

silicone rubbers and elastomer polysiloxanes, natural rubber, polybutadiene, styrene-butadiene, butyl rubber, for example;

polymers such as polyethylene, polypropylene, polystyrene, polyvinylchlorides, polyvinyl acetate, ethacrylate and methacrylate polymers and copolymers and the like.

For wound dressings it is preferred to use silicone rubbers of membrane thickness as will be described.

A usable primer is an aminofunctional silane coupling agent such as N-(2-aminoethyl)-3-aminopropyltrimethoxysilane, available as Dow Corning® Z-6020 Organofunctional Silane. This primer also bonds well to materials such as nylon, dacron and the like, the latter may optionally be components of the substrate, as will be apparent with the description of burn wound dressings and the prostheses to be described. Another material which may be used is an amino-functional silane, e.g., aminoalkylsilanes such as gamma-aminopropyltrietholysilane. Such as material is commercially available from Union Carbide Corporation under the designation Union Carbide® A-1100. Other aminofunctional silanes are also well known in the art, such as aminoalkylsilanes, for example, gamma-aminopropyltriethoxysilane, gamma-aminopropyltrimethoxysilane, N'-(beta-aminoethyl)-N-(beta-aminoethyl)-gamma-aminopropyltrimethoxiysilane, to mention only a few.

Other materials which may be used include hydroxyfunctional silanes, mercapto-functional silanes and other silanes which may react with the substrate at one end of the silane (through an alkoxy group for example) and the other end of which may be coupled to the biological, as will be described.

A typical aminofunctional silating primer and its application are as follows:

Four milliliters of the aminofunctional silating agent was added to 4 milliliters of absolute methyl alcohol along with 0.32 milliliters of distilled water and the resultant material was allowed to sit overnight at room temperature. To the primer solution 69 milliliters of absolute methyl alcohol was added to make a dipping solution into which silicone rubber membranes were dipped for 3-5 seconds. The membranes were then dryed in an oven at 100°-110° C. for 40 to 60 minutes. In the case of breast implants having an outer silicone envelope, with or without other components attached, the implant was completely immersed beneath the surface of the solution and treated as described. The result is a substrate having primary amino functional groups thereon for further reaction as will be described.

Primary or secondary amine functional groups may also be attached to a substrate by physically entrapping an alky amine in the substrate (i.e. dodecylamine or other organic primary or secondary amines). Other materials which may be used include alkanols, alkyl mercaptans, and preferably those compounds which contain an alkyl radical having at least 7 carbon atoms. For example, using a silicone rubber, a solvent in which the amine will dissolve and which causes the rubber to swell, a substrate may be formed with amine functional groups trapped therein and thereon. In a typical example, 4% by volume of dodecylamine (by volume) was dissolved in a 60:40 solvent mixture of toluene and isopropyl alcohol. The substrate was immersed in the amine solution, at room temperature, for 5-8 seconds and then allowed to dry at room temperature for an additional 10-20 minutes. The result is a substrate wherein primary or secondary amine functional groups are attached and available for further reaction.

In the case of burn wound dressings, which represent a preferred form of this invention, the substrate preferably is in the form of a thin rubber membrane-fabric composition which is stretchable in all directions and which has a water vapor transmission rate of between 6 to 12 grams per hour per square foot. Also, the burn covering substrate should be sufficiently strong so that in normal handling and use it does not tear.

A typical burn covering substrate material may be prepared as follows:

A dispersion of 13% dimethylsiloxane elastomer is layered with a precision layering tool at a uniform thickness of 0.006, 0.008, 0.010, 0.012, 0.014, 0.016, 0.018 or 0.020 inches thick plus or minus 0.0003 inches over a MYLAR (polyethylene terephthalate) support member. A typical silicone rubber which may be used is that available from Dow Corning as Q7-2213. After deposition of the dispersion, a finely knitted fabric (dacron or nylon), of 25 denier or less is laid over the wet silicone rubber The fabric is preferably one which is stretchable to 100% or more elongation in all directions. The uncovered composite is allowed to sit at room temperature for 15 minutes and then transferred and cured in an oven at 150° C. for about one hour. The cured composite, still on the support is then stored until processing for binding biologicals thereto.

After curing, the thickness of the silicone rubber is 0.0006, 0.0008, 0.00010, 0.0012, 0.0014, 0.0016, 0.0018 or 0.0020 inches plus or minus 0.0003 inches. Thickness of 0.0008, 0.0010 and 0.0012 inches are preferred for burn dressing membranes. Prior to chemical modification the cured composite may be removed from the MYLAR® support, without the use of release agents, by immersing the support and composite in a 60:40 toluene and isopropyl alcohol solution for 10 minutes at room temperature. The composite is gently pulled off the support and allowed to air dry prior to modification.

The above described composite is a substrate, stretchable in all directions, and having a water vapor transport rate in the range noted and adaptable to modification. The fabric is located at the face of one side of the membrane, i.e partly imbedded in the membrane with portions of the fabric exposed. In use, the fabric side is applied over the woundside so that the fabric faces wound.

Attachment of biologicals to the burn dressing involves first attachment of primary or secondary amine groups on one or both sides of the composite. This may be done by either of the procedures already described. Regardless of the procedure, it is noted that amine groups are present on the exposed fabric surface side as well as on the exposed membrane surface side.

The next step in accordance with this invention, regardless of the nature of the substrate, is to activate the amine functional groups. The preferred procedure in accordance with this invention is as follows:

A saturated solution of cyanuric chloride in acetone is prepared and chilled to 0° C. The substrate (silicone rubber-fabric composite with attached amine functional groups) is then immersed in the chilled solution for 10 seconds. As a result, a bond through the amine to cyanuric chloride at the site of one of the chlorides is formed so that there is now available two chloride groups on the cyanuric chloride available for further reaction.

While the use of cyanuric chloride is preferred because it is more reactive, it is also possible to activate the amine functional groups by reaction with a dialdehyde, such as glutardialdehyde. U.S. Pat. No. 3,810,781 described the use of this material to stabilize heparin ionically bound to a substrate containing a positively charged amine, i.e. the heparinized surface is subsequently treated with the dialdehyde. In contrast, the present invention reacts the amine with the dialdehyde to provide reactive aldehyde group covalently bound to amine-substrate surface.

Thus, a typical procedure involves incubating a substrate with the primary or secondary amine thereon, formed as described by either of the previous procedures, in a 0.5% solution of glutaraldehyde solution, 1/15M disodium hydrogen phosphate, pH 8.2–8.3 for 2–3 hours at room temperature. The result is a substrate in which the primary or secondary amine has reacted with one of the aldehydes of glutaraldehyde to form a Schiff Base covalent bond leaving the other primary or secondary amine containing compounds.

Linkage of the biological may be accomplished one of several ways, depending upon the nature of the biological and the type of amine activation. For example, in the case of proteins, a 0.5–2.0% solution of the protein in 1/15M disodium hydrogen phosphate solution is prepared, pH 8.2–8.3 and the activated substrate is taken directly from the glutaraldehyde activating solution submerged and incubated in the protein solution for 2–8 hours at 25°–55° C. The amine-silicone-fabric composite material can also be activated by cyanuric chloride and biologicals bound by being taken from the saturated cyanuric chloride solution and incubated in a protein solution as described. Essentially the same procedure is used for attachment of mucopolysaccharides to the substrate surface (e.g.: a 0.5% buffered solution thereof as described, and incubated as described).

Depending upon the route taken the biological is covalently bonded through the primary or secondary amine groups of the biological, through the aldehyde to the amine to the substrate. In the case of cyanuric chloride activation, the primary or secondary amine or hydroxyl groups of the biological is covalently coupled through the cyanuric chloride to the amine to the substrate.

By way of illustration of the products of the present invention and the unique character of the biologically activated materials which are bio- and blood compatible, various products were prepared and evaluated as burn dressings in terms of adhesion to animals. The test involved removing the skin of the test animal (rats) and testing the adherence of various products to the subdermal facial tissue. Circular test coupons of 6 mm in diameter were prepared from each material type and the discs were applied at ten different locations on each of the test animals. After 5 hours, the force in grams necessary to remove each of the discs was measured by a tensiometer and adherence was recorded in grams/cm$^2$. The test was repeated for a 72 hour adhesion period and the data again collected. (Details of the test methodology is described by Tavis et al., Annals of Surgery, Vol. 184, No. 5 pg. 594–600, 1976).

As a basis for comparison, products of the present invention were compared with homograft, pigskin and modified bovine collagen membrane, the material with the highest adherence was assigned a value of 100 and other materials were normalized on the basis of their adherence value. All samples were ranked in overall adherence both at 5 hours and 72 hours. The following codes were used to describe each of the products of this invention and the materials evaluated for adherence.

The material code is a series of three letters, x x x, the first letter describing the substrate; the second letter, the activating agents/bonding agent(s); and the third, the biological component bonded to the surface.

The activating agent(s)/bonding agent(s) code is as follows:

A. Dodecyl amine, glutaraldehyde treatment of amine.

B. Silated by coating, glutaraldehyde treatment of amine.

C. Dodecyl amine, cyanuric chloride activation.

D. Silated by coating, cyanuric chloride activation.

E. Dodecyl amine.

F. Silated by coating.

G. No activating agents.

The substrate (fabric silicone rubber composite) code is as follows:

A Edwards membrane -cotton gauze/silicone rubber (see infra).

B. 18/3 nylon fabric 300%×50% elongation.

C. 18/3 nylon fabric 150%×240% elongation.

D. Silicone rubber without fabric.

The code for the biological component bonded to the activated surface, is as follows:

| | | | |
|---|---|---|---|
| A. | Heparin | I. | Alanine |
| B. | Chondroitin sulfate C | J. | Glutamic Acid |
| C. | Egg albumin | K. | Glycine |
| D. | Collagen (tropocollagen-rat skin) | L. | Glyclglycine |
| E. | Lysine | M. | Human albumin |
| F. | Fibrinogen | N. | Gelatin (Porcine Skin) |
| G. | Hemiglobin | O. | Nothing |
| H. | Aspartic Acid | P. | Lecithin |

Overall, the test involved evaluation of a multiplicity of materials, including those presently in use, for the purpose of establishing adherence of products of the present invention for use as burn dressings. Those materials such as the Edward Membrane formerly made by Edwards Laboratories A Division of Amer. Hosp. Supply Corp. and Pigskin, homograft and Collagen membrane formerly made by Edwards Laboratories offer a basis for comparing the adherence of the products of this invention with those recognized in the field as being of use as burn dressings. The Edwards membrane is a composite of a silicone rubber polymer backing and a non-elastic cotton gauze facing and having a substantial thickness variation (0.0005–0.0020 inches thick) as compared to the thin membrane material substrates of the present invention. Further the Edwards membrane is not as stretchable as the substrates of the present invention, the latter preferably having greater than 100% elongation in all directions. Moreover, the Edwards membrane is not biologically activated, although as a basis of comparison, this membrane was used as a substrate and activated in accordance with this invention. Collagen membrane has a cotton gauze component the same as the Edwards material.

In the test, with the exception of homograft and pigskin, which do not include fabric, all substrates were applied with the fabric side in contact with the dorsal facial surface of the test animal. The circular coupons were applied principally to the backs of the test rats to prevent them from being reached and possibly eaten by the test animals. In some instances the patches were scraped loose when the animals contacted the cage walls in their normal movements in the cages. Where this occurred, a value of zero was used and totaled and averaged in the data.

TABLE I

ADHERENCE DATA SUMMARY
5 hr. Adherence Test

| Rank | Sample # | Material | Adherence (gm/cm$^2$) | % Maximum Adherence | # Adhering of 10 Samples Placed |
|---|---|---|---|---|---|
| 1 | 25 | Homograft | 167 | 100 | 8 |
| 2 | 23 | Collagen M. | 133 | 80 | 7 |
| 3 | 24 | Pigskin | 116 | 69 | 9 |
| 4 | 2 | ACC | 99 | 59 | 9 |
| 5 | 19 | BDC | 95 | 57 | 6 |
| 6 | 14 | ADK | 86 | 51 | 8 |
| 7 | 1 | ADC | 82 | 49 | 8 |
| 8 | 13 | ADE | 68 | 41 | 9 |
| 9 | 11 | ADD | 63 | 38 | 9 |
| 10 | 8 | ACK | 59 | 35 | 9 |
| 11 | 18 | BCC | 54 | 32 | 6 |
| 12 | 9 | ACG | 52 | 31 | 9 |
| 13 | 12 | ADB | 51 | 31 | 8 |
| 14 | 17 | ABC | 49 | 29 | 7 |
| 15 | 10 | ADR | 49 | 29 | 8 |
| 16 | 20 | BCD | 47 | 28 | 7 |
| 17 | 15 | ADG | 44 | 26 | 9 |
| 18 | 22 | BDC$_2$ | 44 | 26 | 9 |
| 19 | 21 | DBB | 42 | 25 | 8 |
| 20 | 16 | AAC | 31 | 19 | 6 |
| 21 | 5 | ACD | 30 | 18 | 9 |
| 22 | 4 | ACF | 30 | 18 | 10 |
| 23 | 3 | ADC | 28 | 17 | 9 |
| 24 | 7 | ACE | 26 | 16 | 8 |
| 25 | 6 | ACB | 22 | 13 | 9 |
| MEAN ± STD. DEV. | | | 62.7 ± 36 | 28 ± 25 | 8.2 ± 1.1 |

TABLE II

ADHERENCE DATA SUMMARY
72 hr. Adherence Test

| Rank | Sample # | Material | Adherence (gm/cm$^2$) | % Maximum Adherence | # Adhering of 16 Samples Placed |
|---|---|---|---|---|---|
| 1 | 13 | ADE | 524 | 100 | 10 |
| 2 | 25 | Homograft | 512 | 98 | 6 |
| 3 | 14 | ADK | 499 | 95 | 10 |
| 4 | 6 | ACB | 498 | 95 | 11 |
| 5 | 17 | ABC | 483 | 92 | 11 |
| 6 | 23 | Collagen M. | 472 | 90 | 6 |
| 7 | 12 | ADB | 457 | 87 | 10 |
| 8 | 15 | ADG | 455 | 87 | 8 |
| 9 | 18 | BCC | 455 | 87 | 14 |
| 10 | 20 | BCD | 499 | 86 | 13 |
| 11 | 16 | AAC | 435 | 83 | 10 |
| 12 | 24 | Pigskin | 424 | 81 | 5 |
| 13 | 3 | ADC | 420 | 80 | 9 |
| 14 | .5 | ACD | 419 | 80 | 10 |
| 15 | 2 | ACC | 399 | 76 | 12 |
| 16 | 21 | BDD | 395 | 75 | 6 |
| 17 | 11 | ADD | 392 | 75 | 13 |
| 18 | 9 | ACG | 379 | 72 | 10 |
| 19 | 10 | ADF | 372 | 71 | 11 |
| 20 | 8 | ACK | 339 | 65 | 10 |
| 21 | 19 | BDC | 335 | 64 | 12 |
| 22 | 1 | ADC$_2$ | 328 | 61 | 10 |
| 23 | 22 | BDC$_2$ | 272 | 52 | 9 |
| 24 | 7 | ACE | 246 | 47 | 8 |
| 25 | 4 | ACF | 244 | 47 | 6 |
| MEAN ± STD. DEV. | | | 408 ± 79 | 78 ± 15 | 9.6 ± 2.4 |

TABLE III

ADHERENCE DATA SUMMARY
5 hr. Adherence Test

| Rank | Sample # | Material | Adherence (gm/cm$^2$) | % Maximum Adherence | # Adhering of 10 Samples Placed |
|---|---|---|---|---|---|
| 1 | 22 | BDH | 389 | 100 | 9 |
| 2 | 24 | Collagen M. | 378 | 97 | 10 |
| 3 | 16 | BDK | 297 | 76 | 10 |
| 4 | 6 | BDO | 287 | 74 | 8 |
| 5 | 10 | BDF | 283 | 73 | 8 |
| 6 | 25 | Homograft | 269 | 69 | 10 |
| 7 | 13 | BCM | 261 | 67 | 10 |
| 8 | 21 | BCH | 244 | 63 | 10 |
| 9 | 4 | BFO | 230 | 59 | 9 |
| 10 | 18 | BDL | 230 | 59 | 10 |
| 11 | 17 | BCL | 216 | 56 | 9 |
| 12 | 2 | AGO | 191 | 49 | 9 |
| 13 | 12 | BDC | 180 | 46 | 10 |
| 14 | 3 | BEO | 177 | 46 | 2 |
| 15 | 19 | BCE | 177 | 46 | 10 |
| 16 | 1 | BGO | 173 | 44 | 9 |
| 17 | 14 | BDM | 163 | 42 | 10 |
| 18 | 5 | BCO | 158 | 41 | 10 |
| 19 | 9 | BCF | 149 | 38 | 7 |
| 20 | 15 | BCK | 145 | 37 | 10 |
| 21 | 20 | BDE | 145 | 37 | 10 |
| 22 | 11 | BCC | 134 | 34 | 10 |
| 23 | 7 | BCD | 120 | 31 | 9 |
| 24 | 8 | BDD | 113 | 29 | 10 |
| 25 | 23 | Pigskin | 85 | 22 | 8 |
| MEAN ± STD. DEV. | | | 208 ± 78 | 53 ± 20 | 9 ± 2 |

TABLE IV

ADHERENCE DATA SUMMARY
72 hr. Adherence Test

| Rank | Sample # | Material | Adherence (gm/cm$^2$) | % Maximum Adherence | # Adhering of 16 Placed Samples |
|---|---|---|---|---|---|
| 1 | 4 | BFO | 601 | 100 | 8 |
| 2 | 9 | BCF | 584 | 97 | 2 |
| 3 | 6 | BDO | 548 | 91 | 7 |
| 4 | 18 | BDL | 527 | 88 | 3 |
| 5 | 19 | BCE | 520 | 87 | 11 |
| 6 | 15 | BCK | 509 | 85 | 6 |
| 7 | 13 | BCM | 502 | 84 | 10 |
| 8 | 21 | BCH | 495 | 82 | 11 |
| 9 | 5 | BCO | 467 | 78 | 7 |
| 10 | 8 | BDD | 463 | 77 | 7 |
| 11 | 7 | BCD | 460 | 77 | 7 |
| 12 | 2 | AGO | 431 | 72 | 5 |
| 13 | 11 | BCC | 431 | 72 | 10 |
| 14 | 24 | Collagen M. | 417 | 69 | 11 |
| 15 | 14 | BDM | 410 | 68 | 9 |
| 16 | 12 | BDC | 389 | 65 | 12 |
| 17 | 10 | BDF | 382 | 64 | 4 |
| 18 | 20 | BDE | 378 | 63 | 11 |
| 19 | 23 | Pigskin | 375 | 62 | 12 |
| 20 | 17 | BCL | 357 | 59 | 5 |
| 21 | 16 | BDK | 347 | 58 | 8 |
| 22 | 25 | Homograft | 336 | 56 | 8 |
| 23 | 1 | BGO | 332 | 55 | 2 |
| 24 | 22 | BDH | 308 | 51 | 8 |
| 25 | 3 | BED | 304 | 51 | 5 |
| MEAN ± STD. DEV. | | | 435 ± 85 | 72 ± 14 | 7.6 ± 3 |

TABLE V

| Material | Number of Animals (Rats) | Average Starting Weight (gms) | Percent Mortality (3 Wks) | Average Weight Gain (gms/day) and Correlation with Time (r) | | Relative Synthetic Skin Performance (Adherence and Conformance/100 max. Value) | | |
|---|---|---|---|---|---|---|---|---|
| | | | | (gms/Day) | (r) | WK-1 | WK-2 | WK-3 |
| BDK | 6 | 298 | 33 | .88 | .65 | 52 | 29 | 23 |
| BFO | 5 | 298 | 20 | −.38 | −.44 | 53 | 20 | 20 |
| BDE | 8 | 290 | 37.5 | 1.0 | .95 | 60 | 35 | 28 |
| BDH | 5 | 298 | 60 | 1.1 | .86 | 54 | 20 | 0 |
| BDC | 6 | 276 | 16.7 | 1.35 | .96 | 61 | 33 | 25 |
| BDL | 6 | 269 | 16.7 | 1.39 | .97 | 60 | 32 | 28 |
| BCC | 7 | 278 | 57 | 1.41 | .82 | 81 | 53 | 50 |
| BCH | 5 | 329 | 0 | 1.85 | .99 | 76 | 45 | No |

TABLE V-continued

| Material | Number of Animals (Rats) | Average Starting Weight (gms) | Percent Mortality (3 Wks) | Average Weight Gain (gms/day) and Correlation with Time (r) | | Relative Synthetic Skin Performance (Adherence and Conformance/100 max. Value) | | |
|---|---|---|---|---|---|---|---|---|
| | | | | (gms/Day) | (r) | WK-1 | WK-2 | WK-3 |
| MEAN ± STD. DEV. | 6 ± 1.1 | 292 ± 18.8 | (2 wks) 30 ± 21 | 1.1 ± .66 | .72 ± .48 | 62 ± 11 | 35 ± 10 | Data 25 ± 15 |

The data in Table V represents the results of a test in which the best materials, based on adherence data were placed on 20% full thickness dorsal defects of rats. Evaluations were made each week and values assigned for adherence and conformity, as follows:

| Membrane Adherence | Membrane Conformity |
|---|---|
| 1. No adherence | 1. No observation--non-adherent |
| 2. Minimal | 2. Minimal adherence with ridges and ripples |
| 3. Moderate | 3. Moderately adherent with ridges and ripples |
| 4. Mostly adherent | 4. Mostly adherent with ridges and ripples |
| 5. Very adherent | 5. High conformity and adherence. |

On the basis of the above data and further testing it was found that the bio- and blood compatible materials of the present invention when structured for use as a burn dressing optimally includes a substrate which is substantially stretchable, compliant, and comformable. A preferred material is, accordingly, material C (18/3 nylon fabric 150%×240% elongation) primarily because of the ability of the substrate to stretch and conform to the area of application.

In combination therewith, it is preferred to use a bonding agent such as dodecyl amine which is cyanuric chloride (C) activated with gelatin (porcine skin) coupled thereto. Also useable is a coated silating material (D).

By way of example, a comparison of the preferred burn dressing with the accepted standard demonstrate the performance of the preferred material:

| Material | Performance | No. of Animals |
|---|---|---|
| Pigskin | 87.2 ± 11.4 | 14 |
| CCN | 97.6 ± 4.6 | 12 |
| CDN | 91.2 ± 9.6 | 16 |

The above data are significant in establishing the superiority of these fabricated materials over the others and those naturally available when used as burn dressings. It is to be understood, however, that other combinations of components may be preferred based on other ultimate uses of the materials of this invention.

Although coupling of the biological has been described, under proper conditions other techniques, known in the art may be used, see for example "Immobilized Enzymes For Industrial Reactors", Messing, Academic Press, N.Y. 1975, pages 99–123. The preferred system, however, is that as set forth herein.

The above described materials, especially those of Table V and CCN and CDN represent the better of the group prepared for use as burn dressings, the test data on rats established the ability of the better materials to remain adherent with nearly complete connective tissue ingrowth and without superation for periods up to one month.

The materials are easily packaged, easily sterilized by appropriate procedures and possess a relatively long shelf life.

It will also be apparent from the foregoing description that the products are relatively easily fabricated since the effective chemical reactants are easily attached by appropriate chemical bonds to various substrates. Since the reactions are relatively fast and controllable, selected surface portions or all surface portions may be treated to provide one or more zones of various desired biologicals.

Further, preliminary data on several of the specific biologicals indicates that the materials are non-extractable, free of bio- and blood extractable contaminants and non-antigenic.

In the case of burn dressings, an important practical application of the present invention, the novel substrate in membrane form which is stretchable and compliant and thus easily fits in a variety of body contours, offers unique advantages over prior materials. Also, the effective attachment of effective biologicals provides for adherence to the wound site over extended periods, with proper water vapor transport through the membrane, important characteristics in burn therapy for dressings of this type.

Prostheses in accordance with this invention, and especially breast prostheses, include a three dimensional substrate of an appropriate shape and configuration. The shape and configuration may be as previously described. For example, in the case of mammary prostheses, the implant may be a hollow envelope of silicone rubber filled with a silicone gel or with normal saline solution, although silicone gel is preferred. The filler or core is preferably soft, but not unduly soft material, and one which is malleable and contained within an impervious envelope as is known in the art. As is also known in the art, an implant having an outer porous surface may be used as well as any of the variants described in the Naficy and Rybka patents previously identified.

In addition to the biologicals already identified, certain materials are preferred as biologicals in the case of mammary prostheses. One such material is Collagen Gelatin Type A of comparatively low molecular weight in the range of 7,000 to 27,000 molecular weight units. Another type of material is a higher molecular weight Collagen Gelatin Type A in the range of 10,000 to 300,000 molecular weight units. Also usable is glycosaminoglycan (GAG), i.e., a mixture of 4- and 6-chrondroitin sulfate of 99% purity. Heparin may also be used and is preferred to GAG.

More specifically, three unique collagenous preparations termed A, HMW and LMW may be used for surface modification of the mammary prosthesis. Preparation A is obtained commercially as gelatin Type A, 250 Bloom strength, and may be used without further processing. The HMW material is derived from the A material and is enriched in high molecular weight components. The LMW material is also derived from a gelatin Type A of 75 Bloom strength and contains only comparatively low molecular weight components.

Molecular sieve chromatography, using agarose, demonstrates that the A material contains compounds of 300,000; 190,000; 7,000; 47,000; 32,000; 16,000; and 8,000 daltons. The first three compounds correspond closely to classical gamma, beta and alpha collagen chains and were interpreted as such. The A material is largely a collective of peptides of 97,000 daltons and larger, the smaller compounds making up only a small portion of the A material.

The HMW material, again based on molecular sieve chromotography appears devoid of 32,000; 16,000 and 8,000 dalton peptides and is nearly devoid of the 47,000 dalton peptide while is also reduced in alpha component content, although the beta and gamma components and the larger components of the A material are present. By contrast, the LMW material consists of a narrow distribution of peptides of a mean molecular weight of 13,000 daltons.

The glycosaminoglycan component, GAG used in this work, is specifically a mixture of chondroitin 4 and 6 sulfate. The heparin. component used in this work is a standard commercial preparation sold by Sigma and is characterized as the sodium salt of heparin from porcine intestinal mucosa, 151 USP K units.

In the following description, the silating agent referred to as "Aminosilane Z" was N-(2-aminoethyl)-3-aminopropyltrimethoxysilane obtained from Dow Corning Corporation as DOW CORNING ® Z-6020 Organofunctional Silane.

Various prostheses were prepared as follows:

I. Surface Preparation

A. Dodecylamine as the amine source

1. The silicone surface was washed with Ivory detergent, followed by Isopropyl Alchohol (IPA).
2. The washed surface was treated with 4% dodecylamine (by volume) 1:1 Toluene:IPA (v:v) for 10 min. The dodecylamine was warmed to obtain the liquid state.
3. The surface was air dried and treated for 5 min. in acetone.
4. The material was then treated with 5% cyanuric chloride (w:v) in acetone 30 min. and rinsed twice with acetone.
5. The surface was then treated with biological (protein or complex carbohydrate) immediately after the surface was air dried.

B. Aminosilane Z as the amine source ("Primer Z")

1. The "primer" was prepared by combining 4 ml Aminosilane Z, 4 ml absolute methanol and 0.32 ml distilled $H_2O$, mixed vigorously, and allowed to stand overnight at room temperature. The solution should remain liquid; if it gelled it was not used.
2. 69 ml absolute methanol was added to the "primer".
3. The cleaned surface was dipped into above solution 3-5 sec.
4. Thereafter the surface was dipped in absolute methanol 1 sec, and cured 60 min., 110° C.

After cooling to room temperature, the surface was treated with cyanuric chloride as per IA4-5.

II. Attachment of Biological to Surface

A. Gelatin A

1. Using heat (approximately 45° C.) a 0.1% solution of Type A gelatin 250 Bloom strength (Kind and Knox) in 0.025M $Na_2HPO_4.7H_2O$, pH 9.5 was prepared.
2. The prepared surface was treated with this protein solution for 1½ hrs. at room temperature.
3. The surface was submerged in boiling distilled water 10 min. and rinsed twice in 50° C. distilled water, followed by air drying at room temperature.

B LMW

1. A LMW material by molecular sieve chromatography of gelatin of Type A 75 Bloom gel strength was treated as follows:
   a. Using heat (45°-50° C.) 100 mg "gelatin 75" was dissolved in 10 ml 1M $CaCl_2.2H_2O$, 0.05M Tris, pH 7.4, 2M guanidine hydrochloride. Heating was continued for 45 minutes.
   b. The cooled sample was chromatographed on a 2.5×45 cm column of BioGel Al-5m, 200-400 mesh (BioRad) previously equilibrated with 1M $CaCl_2.2H_2O$, 0.05M Tris, pH 7.4. The sample was eluted with the same buffer at 1 ml/min flow rate. The column was monitored at 230 nm. During the run, the first 165 ml eluted from the column was discarded, the next 35 ml eluted was collected as LMW. This material represented the back side of the major protein peak eluted, and had a molecular weight of 10,000-13,000.
   c. The pH of the LMW was adjusted to 9.5.
2. The prepared surfaces were treated 1½ hr. with LMW.
3. Preparation continued as per IIA3.

C. Heparin or Chondroitin Sulfate

1. A solution of 0.01 NaOH, pH 11.0 was prepared.
2. Sufficient heparin (Sigma, sodium salt, grade II) or chondroitin sulfate (Sigma, grade III) was added to yield a 1-2% solution, and the pH adjusted to 11.0.
3. The prepared surface was treated with the above solution ½ hr. at 70° C.
4. The material was washed with 1M NaCl, 5 min. room temperature, then rinsed with distilled water and air dried at room temperature.

These above procedures yielded 0.25-0.50 ug biological per $cm^2$ surface area.

The various samples are set forth in Table M-1.

TABLE M-1

| Sample No. | Substrate Type | Filler Type | Activation/ Bonding | Biological Type |
|---|---|---|---|---|
| 2* | silicone elastomer | gel | dodecylamine/cyanuric chloride | gelatin Type A, 250 Bloom strength |
| 3 | silicone elastomer | saline | silylated by coating with Primer/ cyanuric chloride | same as 2 |
| 4 | silicone | gel | as per 3 | same as 2 |
| 5 | silicone | gel | as per 2 | low molecular weight (LMW) gelatin Type A, 75 Bloom strength |
| 6 | silicone | gel | as per 2 | GAG |
| 7 | silicone | gel | as per 2 | heparin |

TABLE M-1-continued

| Sample No. | Substrate Type | Filler Type | Activation/ Bonding | Biological Type |
|---|---|---|---|---|
| 8 | silicone | gel | none-control | none-control |
| 9 | silicone | saline | none-control | none-control |

*no sample 1 in series

The materials of Table M-1 were tested in animals in accordance with the following protocol which is a variant of that described in Plastic and Reconstructive Surgery, 68(6), pp. 905–912 (December, 1981).

Male guinea pigs (Cavia Porcellus) of the White English Hartley strain were used each in a weight range of 300–450 grams. Guinea pigs were selected based on the data of Rybka, F. J., Plastic & Recon. Surg., 66:507–508, 1980. There were 20 animals for each test group 2–9 and each test animal was identified by ear tags. The scalp area of each young adult guinea pig was chosen as the experimental site because it is the area of the rodent's body which most closely mimics the human chest wall topography.

Hand contact with the implants used in the test was avoided and only implants having tonometer readings equivalent to 6 to 20 mm Hg were used. The mini-mammary implants (a 1.75 cc volume hollow silicone rubber container filled with silicone gel or saline) were sterilized in an autoclave at 121° C. (;Kg/cm) for 15 minutes. Saline filled implants were placed in polycarbonate autoclave bags, submersed in saline, heat sealed and autoclaved as described.

The guinea pigs were anesthesized with a Ketamine/Xylazine combination (5 mg/Kg, 1 mg/Kg) and following onset of anesthesia, their heads and necks were clipped free of hair and disinfected with a solution of Phemoral. Using sterile techniques a 2.5 cm incision was made on the dorsum of each animals neck and a subcutaneous pocket was blunt dissected 2.5 cm cephalic to the incision using a pair of hemostats. The pocket was made from the base of one ear to the other. The implant was then inserted into the pocket and an absorbable internal stitch was placed 1 cm caudal from the implants. The wound was then closed with 3 to 4 individual stitches using a No. 4-0 silk suture. After the surgical procedure each animal was returned to a cage and allowed to recover. The implants remained in place for eight (8) weeks.

The animals were observed twice a day until fully recovered from anesthesia and once a day thereafter.

At the conclusion of eight weeks, each animal was anesthetized with methoxyflurane and the implant and surrounding capsule was carefully dissected from adjacent structures without rupture. The shape of the implant and the surrounding capsule and its location was noted and recorded. The weight of the capsule was determined and tonometer readings (minimum of three) were taken using a 37 g counterweight as a constant. The capsule was separated from the implant and a portion of each capsule was preserved in the following two solutions:

a. Phosphate buffer (small pH 7.4 at 37° C.) oxygenated with 95% oxygen and 5% $CO_2$ for in vitro analysis of contracting structures.

b. 1:1 solution of 5% glutaraldehyde/paraldehyde for microscopic and chemical analysis and capsule thickness measurements.

To test the contractile characteristics of the capsular tissue, one half of the dissected capsule (strips measuring about 2.0 by 0.5 cm were used). One end of the tissue strip was suspended from the end of the frontal level of a Stratham strain guage and the other end attached to the bottom of a double wall glass bath. The bath contained 100 milliliters of Tyrode's solution kept at. 37° by means of a thermostatically controlled circulating water pump. A mixture of 95% oxygen and 5% $CO_2$ was bubbled through the solution to keep the tissue sample viable. All tissues were tested within 30 minutes from the removal of the animals.

The tissue strip was allowed to stabilize and an agonist drug 5-hydroxytryptamine, was added to the bath solution (final concentration at $1 \times 10^{-5}$ G/ml). The vertical displacement was amplified and recorded on a Beckman dynograph. If a contracting response was obtained, the strip of tissue was treated with Papaverine hydrochloride (at $1 \times 10^{-5}$ G/ml.) to determine if relaxation occurred. If contraction did not occur, an additional quantity of 5-hydroxytryptamine was added ($5 \times 10$ G/ml) to further try to induce contracture. If contraction was observed, the tissue strip was then treated with Papaverine hydrochloride.

The data from the 20 animals of each of the eight tests was assembled and analyzed statistically. The results of that statistical analysis is set forth in the following Table M-2, while Table M-3 presents data, again in statistical format related to the various parameters shown in the headings of the various columns.

TABLE M-2

| Sample # Type | Magnitude of Contracture | | Frequency of Contracture |
|---|---|---|---|
| | All Data | All Data Except Highest Value | |
| #7 GEL-HEP A ($\overline{X} \pm S$)* | .921 ± 1.995 | .528 ± 1.05 | C*** 22.2 |
| AMINE B X** | 50.3 ± 100 | 3.74 ± 118 | D**** 29 |
| #6 GEL-GAG A | 1.28 ± 1.59 | 1.03 ± 1.17 | C 47.4 |
| AMINE B | 69.9 ± 79.9 | 73.0 ± 132 | D 62 |
| #2 GEL-COLLAGEN A | .775 ± 1.45 | .553 ± 1.08 | C 21.1 |
| AMINE B | 42.3 ± 72.9 | 39.2 ± 121 | D 27.6 |
| #5 GEL-LMW A | 1.02 ± 1.37 | .85 ± 1.2 | C 38.9 |
| COLLAGEN-AMINE B | 55.7 ± 68.8 | 60.3 ± 135 | D 50.1 |
| #4 GEL-COLLAGEN A | .17 ± .48 | .09 ± .36 | C 5.9 |
| SILATED B | 9.3 ± 24.1 | 6.4 ± 40.4 | D 7.7 |
| #8 GEL A | 1.83 ± 1.99 | 1.41 ± .89 | C 76.5 |
| CONTROL B | 100 ± 100 | 100 ± 100 | D 100 |
| #9 SALINE A | 2.30 ± 3.55 | 1.58 ± 1.53 | C 60.0 |
| CONTROL B | 126 ± 178 | 112 ± 172 | D 78.4 |
| #3 SALINE-COLLAGEN A | .786 ± 2.42 | .154 ± .555 | C 14.3 |

TABLE M-2-continued

| Sample # Type | Magnitude of Contracture | | Frequency of Contracture |
|---|---|---|---|
| | All Data | All Data Except Highest Value | |
| SILATED B | 43.0 ± 122 | 10.9± 62.4    D | 18.7 |

*($\overline{X}$ ± S) = MEAN ± Standard Deviation

**$\overline{X} = \left(\dfrac{\overline{X}\text{ sample}}{\overline{X}\text{ gel contracture}}\right)^{100} \quad S = \left(\dfrac{S\text{ sample}}{S\text{ Gel Contracture}}\right)^{100}$

***$C = F_s$ = Frequency of sample contracture

****$D = F_s/F_c = \dfrac{(\text{Frequency of sample contracture})}{(\text{Frequency of gel control contracture})} \times 100$

TABLE M-3

| Sample | Thickness | Weight | Pressure measurements Post Implantation | | |
|---|---|---|---|---|---|
| | | | Initial Implant | Capsule & Implant | Implant |
| #7 | 70 ± 23 | 196 ± 45 | 15.5 ± 4.4 | 9.06 ± 5.57 | 12.9 ± 4.28 |
| | 69.3 ± 95.8 | 90.7 ± 65.2 | 122 ± 138 | 83.9 ± 206 | 88.4 ± 148 |
| #6 | 75 ± 28 | 240 ± 81 | 13.0 ± 3.87 | 10.7 ± 4.11 | 12.5 ± 3.82 |
| | 74.3 ± 117 | 111 ± 117 | 102 ± 121 | 99.1 ± 152 | 85.6 ± 132 |
| #2 | 80 ± 32 | 243 ± 67 | 11.7 ± 4.2 | 8.28 ± 3.66 | 11.1 ± 4.08 |
| | 79.2 ± 133 | 112 ± 97.1 | 92.1 ± 131 | 76.7 ± 136 | 76 ± 141 |
| #5 | 77 ± 25 | 176 ± 50 | 13.3 ± 3.3 | 9.4 ± 2.6 | 10.3 ± 3.7 |
| | 76.2 ± 104 | 81.5 ± 72.5 | 105 ± 103 | 87 ± 96.3 | 74 ± 128 |
| #4 | 113 ± 59 | 245 ± 73 | 10.3 ± 2.93 | 6.86 ± 3.46 | 7.7 ± 2.5 |
| | 112 ± 246 | 113 ± 106 | 81.1 ± 91.6 | 63.5 ± 128 | 52.3 ± 86.2 |
| #8 | 101 ± 24 | 216 ± 69 | 12/7 ± 3.2 | 10.8 ± 2.7 | 1.46 ± 2.9 |
| | 100 ± 100 | 100 ± 100 | 100 ± 100 | 100 ± 100 | 100 ± 100 |
| #9 | 94 ± 27 | 180 ± 43 | 14.4 ± 4.6 | 18.8 ± 8.57 | 19.0 ± 7.05 |
| | 93 ± 112 | 83.3 ± 62.3 | 113 ± 144 | 174 ± 317 | 131 ± 243 |
| #3 | 106 ± 40 | 203 ± 48 | 13.1 ± 5.29 | 16.5 ± 5.46 | 13.0 ± 6.11 |
| | 105 ± 167 | 94.0 ± 64.6 | 103 ± 165 | 153 ± 202 | 89 ± 211 |

For each test, under the headings of Magnitude of Contracture, there are two readings. The first indicates the mean plus or minus the standard deviation, while the second reading effectively relates all of the data to the standard which is test No. 8, assuming values of 100%. Thus, the second entry under each test and each column in the Magnitude of Contracture was obtained by dividing the mean value for each sample by the mean value for the standard and multiplying the result by 100, while the standard deviation was obtained by using the standard deviation for each sample divided by the standard deviation of the control multiplied by 100. The data appearing under the heading "Frequency of Contracture" provides two different types of information, the one indicating the percentage number of samples in which contracture was noted (item $C=F_s$) while the second percentage ($D=F_s/F_c$) was derived using frequency of contracture of each samples divided by the frequency of contracture of the standard multiplied by $100(F_s/F_c)$. Under the heading Magnitude of Contracture, the column labelled "All Data" utilize all data developed with the exception of those particular instances in which the data was possibly erroneous. The column headed "All Data Except Highest Value" corresponds to the column "All Data", except that the highest value in each set of the data were eliminated to generate the data appearing in this particular column.

The data of Table M-3 are physical measurements related to the capsule thickness in microns, the capsule weight in milligrams, implant pressure was that taken prior to implantation and represents the pressure inside the implant before the surgical procedure. The columns relating to Post Implantation Data represent measurements of the pressure with the capsule attache after removal from the test animals while the heading "Implant" represents the pressure internally of the implant after the surgical procedure and after removal of the capsule.

The gross comparison of the data in table M-2 indicates that, as compared to the gel control, and excluding the saline control, all implants perfomred better than did the gel control. Similarly, all implants performed better than did the saline control.

Again, by way of explanation, the data for the magnitude of the contracture is a measurement of the amount of deflection of a premeasured strip of the capsule in response to the drugs identified in the test procedure.

Listed in Table M-4 are the probabilities of compared responses between treatment groups being the same. These probabilities are derived from the chi square test for independence. A probability value less than 0.05 ($p \leq 0.05$) indicates that the compared responses for the two groups are significantly different. When a dash is indicated in the table, either a comparison could not be made, e.g., gel control versus saline control, or the probability for the compared groups exceeded 0.05 and, therefore, the groups being compared were not statistically significantly different.

TABLE M-4

| Sample | Fill | Response Rate | 8 Gel (78%) | 9 Saline (75%) | 3 Saline (14%) | 4 Gel (11%) | 2 Gel (35%) | 5 Gel (42%) | 6 Gel (60%) | 7 Gel (37%) |
|---|---|---|---|---|---|---|---|---|---|---|
| 8 | Gel | (78%) | — | — | <.001 | <.001 | <.01 | <.05 | — | <.05 |

TABLE M-4-continued

| Sample | Fill | Response Rate | 8 Gel (78%) | 9 Saline (75%) | 3 Saline (14%) | 4 Gel (11%) | 2 Gel (35%) | 5 Gel (42%) | 6 Gel (60%) | 7 Gel (37%) |
|---|---|---|---|---|---|---|---|---|---|---|
| 9 | Saline | (75%) | — | — | <.001 | <.001 | <.05 | <.05 | — | <.05 |
| 3 | Saline | (14%) | <.001 | <.001 | — | — | — | — | <.01 | — |
| 4 | Gel | (11%) | <.001 | <.001 | — | — | — | <.05 | <.01 | — |
| 2 | Gel | (35%) | <.01 | <.05 | — | — | — | — | — | — |
| 5 | Gel | (42%) | <.05 | <.05 | — | <.05 | — | — | — | — |
| 6 | Gel | (60%) | — | — | <.01 | <.01 | — | — | — | — |
| 7 | Gel | (37%) | <.05 | <.05 | — | — | — | — | — | — |

Contracture rates were statistically significantly reduced for the following silated bound biological coated implants when compared to the gel (78%) and saline (75%) filled controls: (1) gel-filled, Gelatin A (11%) and (2) saline-filled, Gelatin A (14%). Statistically significantly reduced contracture rates were also observed for the following gel-filled, dodecylamine bound biological coated implants: (1) Gelatin A (35%), (2) low molecular weight Gelatin A (42%) and (3) heparin (37%).

The contracture rate observed for gel-filled, dodecylamine bound, glycosaminoglycans coated implants (60%) was not significantly reduced when compared to either control.

By way of further characterization of the biologically active surface of the mammary prostheses in accordance with this invention, the "Gelatin Type A" consists of a variety of collagenous peptides, the prominent members of which are the gamma chain (285,000 daltons) the beta and alpha chains (190,000 and 95,000 daltons, respectively), and peptides larger than 300,000 daltons. Also present, in minor amounts, are peptides less than 95,000 daltons.

Test work has indicated that when exposed to a solution of Gelatin Type A, a thin film of gelatin is adsorbed to the silicone surface which may be removed under harsh conditions, such as treatment with 1% sodium dodecylsulfate at 90° C. The surface modification in accordance with the present invention, i.e. covalently cross linking the material to the silicone surface, is remarkably bound, i.e. the cross linked material is non-extractable with 1% sodium dodecylsulfate at 90° C. In the case of the mini-mammary prostheses used in the animal tests, the process of this invention binds 0.25-0.50 mg/cm surface area.

In an attempt to characterize the number of binding sites available for cross linking, radio-label testing was performed using [$^3$H] glycine as the probe. [$^3$H] glycine contains only one amino group and theoretically should bind only to one site. The probe was relatively small and did not sterically interfere with neighboring binding sites and was radioactively labelled in such a way that the tritium was not lost during the reactions. Further, the [$^3$H] glycine solution used was sufficiently concentrated to more than staruate all binding sites without addition of unlabelled carrier glycine.

In the procedure [$^3$H] glycine was bound to 1 cm$^2$ silicone sheets, using the covalent bonding system of this invention. In some cases, the surface was silated using the Aminosilane Z material as the amino source, and in others, dodecylamine was used as the amino source. Appropriate control sheets were also prepared and tested, all sheets being assayed for radioactivity using a liquid scintillation system.

After correction for counter efficiency and specific activity of the probe, analysis of the data indicated that with a silating material such as Aminosilane Z, there were between 6.0 to 6.5×10$''$ binding sites per square cm. By comparison, where dodecylamine was used there were between 0.5–1.6×10$^{10}$ binding sites per square cm. Again for comparison purposes, assuming an average molecular weight of 300,000 daltons for the Gelatin Type A used in the study, it was expected that 1.24 cross links/peptide would form using a silating material such as Aminosilane Z while 0.020 cross links/peptide would form using dodecylane. These data tend to indicate that with a silating material such as Aminosilane Z, essentially all the peptides would be cross-linked to the surface and would be sufficiently bound so as to resist leaching under physiological conditions. By comparison, using dodecylamine, fewer peptides are cross-linked, the remainder apparently being entrapped and entangled by the bound peptides. While the surface would still be biologically active, a portion of the material may, in time, be leached under physiological conditions. These data tend to be confirmed by the animal test data which indicated that the silated surface performed better than did the dodecylamine surface. Both, however, performed better than did the controls in the animal tests.

On the basis of the data generated, it is established that the use of the biological as described significantly improves the performance of the implant from the standpoint of significantly reducing the tendency for the surrounding fibrous capsule to exhibit contracture.

It will, accordingly, be apparent to those skilled in the art that various alterations, changes and modifications may be made with respect to the products and procedures herein described without departing from the scope of the present invention as set forth in the appended claims.

What is claimed is:

1. An implantable breast prosthesis comprising:
   a three dimensional member having an outer surface at least a portion of which is adapted to be in contact with tissue and the like in a host recipient,
   at least said portion of said member having functional groups extending therefrom, said functional group being selected from the group consisting of primary and secondary amino groups,
   said amino groups having attached thereto a reactive group selected from the group consisting of aldehyde and aryl-halide groups,
   a biological having functional groups selected from the group consisting of primary and secondary amino groups and hydroxyl groups being coupled to said portion of said member through reaction between the functional groups of said biological and the aldehyde or aryl-halide groups attached to said primary or secondary amino groups which extend from said portion of said member, and said biological operating to provide bio- and blood compatible qualities to said surface portion.

2. A prosthesis as set forth in claim 1 wherein said member is flexible.

3. A prosthesis as set forth in claim 2 wherein said member is flexible silicone rubber.

4. A prosthesis as set forth in claim 2 wherein said member encloses a malleable core.

5. A prosthesis as set forth in claim 2 wherein said member encloses a core of malleable material, said core of malleable material being a silicone gel.

6. A prosthesis as set forth in claim 2 wherein said biological is a collagen gelatin type A material.

7. A prosthesis as set forth in claim 2 wherein said biological is heparin.

8. A breast prosthesis as set forth in claim 2 wherein said member forms a body member, and said body member being a single lumen prosthesis.

9. A breast prosthesis as set forth in claim 2 wherein said member forms a body member, and said body member being a double lumen prosthesis.

10. A breast prosthesis as set forth in claim 2 wherein said biological is selected form the group consisting of; gelation Type A, high molecular weight gelatin Type A and low molecular weight gelatin Type A.

* * * * *

UNITED STATES PATENT AND TRADEMARK OFFICE
CERTIFICATE OF CORRECTION

PATENT NO. : 4,820,302

DATED : April 11, 1989

INVENTOR(S) : E. Aubrey Woodroof

It is certified that error appears in the above-identified patent and that said Letters Patent is hereby corrected as shown below:

Cover page, Related U.S. Application Data [63], "Ser. No. 370,977, Apr. 22, 1982, abandoned," should read --Ser. No. 370,977, Apr. 22, 1982, Pat. No. 4,828,561,--.

Column 1, lines 7-8, "now abandoned," should read --, now Pat. No. 4,828,561,--.

Column 19, line 7, "7,000" should read --97,000--.

Column 21, line 27, "cm" should read --$cm^2$--.

Column 22, line 43, "(5x10" should read --(5x$10^{-5}$--.

Column 24, line 35, after "milligrams," insert --and pressures expressed in millimeters of mercury. The initial--.

Column 25, Table M-4, Sample 7 line, last entry under Gel (78%) and Saline (75%), "<.05" should read --$\leq$.05--, each instance.

UNITED STATES PATENT AND TRADEMARK OFFICE
CERTIFICATE OF CORRECTION

PATENT NO. : 4,820,302
DATED : April 11, 1989
INVENTOR(S) : E. Aubrey Woodroof

It is certified that error appears in the above-identified patent and that said Letters Patent is hereby corrected as shown below:

Column 26, line 55, Claim 1, "functional group" should read --functional groups--.

Column 28, line 10, Claim 10, "form the" should read --from the--.

Column 28, line 11, Claim 10, "gelation" should read --gelatin--.

Signed and Sealed this

Twenty-sixth Day of February, 1991

Attest:

HARRY F. MANBECK, JR.

*Attesting Officer*      *Commissioner of Patents and Trademarks*